US00PP18443P2

(12) United States Plant Patent
Hofmann

(10) Patent No.: US PP18,443 P2
(45) Date of Patent: Jan. 22, 2008

(54) ***GERANIUM* PLANT NAMED 'PACHAFVEL'**

(50) Latin Name: *Pelargonium peltatum*
Varietal Denomination: Pachafvel

(75) Inventor: Christa Hofmann, Radeburg (DE)

(73) Assignee: Elsner PAC Jungpflanzen, Dresden (DE)

( * ) Notice: Subject to any disclaimer, the term of this patent is extended or adjusted under 35 U.S.C. 154(b) by 0 days.

(21) Appl. No.: 11/358,873

(22) Filed: Feb. 17, 2006

(51) Int. Cl.
*A01H 5/00* (2006.01)

(52) U.S. Cl. ..... Plt./318
(58) Field of Classification Search ..... Plt./318, Plt./332
See application file for complete search history.

(56) References Cited

PUBLICATIONS

UPOVROM Plant Variety database. 2006/04 search for 'Arina'.*

* cited by examiner

*Primary Examiner*—Kent Bell
*Assistant Examiner*—Annette H Para
(74) *Attorney, Agent, or Firm*—C. A. Whealy

(57) ABSTRACT

A new and distinct cultivar of Ivy *Geranium* plant named 'Pacharvel', characterized by its upright, outwardly spreading and trailing plant habit; vigorous growth habit; freely basal branching habit; large, single and bright red-colored flowers; and good garden performance.

2 Drawing Sheets

Botanical designation: *Pelargonium peltatum.*
Cultivar denomination: 'Pachafvel'.

BACKGROUND OF THE INVENTION

The present invention relates to a new and distinct cultivar of Ivy *Geranium* plant, botanically known as *Pelargonium peltatum,* and hereinafter referred to by the name 'Pacharvel'.

The new Ivy *Geranium* is a product of a planned breeding program conducted by the Inventor in Dresden, Germany. The objective of the breeding program was to develop new large Ivy *Geraniums* with attractive flower coloration.

The new Ivy *Geranium* originated from a cross-pollination made by the Inventor in 2001 of two proprietary selections of *Pelargonium peltatum,* not patented. The cultivar Pacharvel was discovered and selected by the Inventor as a flowering plant within the progeny from the stated cross-pollination in a controlled environment in Dresden, Germany in 2002.

Asexual reproduction of the new cultivar by terminal cuttings in a controlled environment in Dresden, Germany since 2002 shown that the unique features of this new Ivy *Geranium* are stable and reproduced true to type in successive generations of asexual reproduction.

SUMMARY OF THE INVENTION

The following traits have been repeatedly observed and are determined to be the unique characteristics of 'Pacharvel'. These characteristics in combination distinguish 'Pacharvel' as a new cultivar and distinguish is from other known Ivy *Geranium* cultivars:

1. Upright, outwardly spreading and trailing plant habit.
2. Vigorous growth habit.
3. Freely basal branching habit.

4. Large, single and bright red-colored flowers.
5. Good garden performance.

Plants of the new Ivy *Geranium* differ primarily from plants of the parent selections in flower coloration.

Plants of the new Ivy *Geranium* can be compared to plants of the cultivar Pachex, not patented. In side-by-side comparisons conducted in Dresden, Germany, plants of the new Ivy *Geranium* differed from plants of the cultivar Pachex in the following characteristics:

1. Plants of the new Ivy *Geranium* were not as vigorous as plants of the cultivar Pachex.
2. Plants of the new Ivy *Geranium* had smaller leaves than plants of the cultivar Pachex.
3. Plants of the new Ivy *Geranium* had smaller flowers than plants of the cultivar Pachex.
4. Plants of the new Ivy *Geranium* and the cultivar Pachex differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Flower and foliage colors in the photographs may differ slightly from the color values cited in the detailed botanical description which accurately describe the colors of the new Ivy *Geranium*. The photograph on the first sheet comprises a side perspective view of a typical flowering plant of 'Pacharvel' grown in a container. The photograph on the second sheet is a close-up view of typical flowers of 'Pacharvel'.

DETAILED BOTANICAL DESCRIPTION

Plants of the cultivar Pacharvel have not been observed under all possible environmental conditions. The phenotype may vary somewhat with variations in environment, such as temperature and light intensity, without, however, any variance in genotype. The aforementioned photographs and following observations and averaged measurements describe plants grown during the spring in containers in Dresden, Germany, and under commercial practice in a glass-covered greenhouse with day temperatures ranging from 18° C. to 20° C., night temperatures about 18° C. and light levels ranging from 15 to 100 kilolux. Plants used for the photographs and the description were about six months old and were pinched three times. In the following description, color references are made to The Royal Horticultural Society Colour Chart, 1995 Edition, except where general terms of ordinary dictionary significance are used.

Botanical classification: *Pelargonium peltatum* cultivar Pacharvel.

Parentage:

*Female, or seed, parent.*—Proprietary selection of *Pelargonium peltatum,* not patented.

*Male, or pollen, parent.*—Proprietary selection of *Pelargonium peltatum,* not patented.

Propagation:

*Type cutting.*—Terminal cuttings.

*Time to initiate roots, summer.*—About 18 days at 22° C.

*Time to initiate roots, winter.*—About 22 days at 22° C.

*Time to produce a rooted young plant, summer.*—About 25 days at 22° C.

*Time to produce a rooted young plant, winter.*—About 30 days at 22° C.

*Root description.*—Fine, fibrous; white, close to 155D, in color.

*Rooting habit.*—Freely branching; dense.

Plant description:

*General appearance.*—Upright, outwardly spreading, trailing and eventually cascading plant habit; uniformly mounded; densely foliated.

*Growth and branching habit.*—Vigorous growth habit. Freely branching habit with about five lateral branches per plant.

*Plant height, to top of umbels.*—About 25 cm.

*Plants height, to top of foliar plane.*—About 20 cm.

*Plant width.*—About 35 cm.

*Lateral branches.*—Length: About 20 cm. Diameter: About 5 mm. Internode length: About 4 cm. Texture: Sparsely pubescent. Color: 144A.

*Foliage description.*—Arrangement: Opposite; simple. Length: About 3 cm. Width: About 6 cm. Shape: Palmately-lobed. Apex: Acute. Base: Cordate; closed. Margin: Lobed. Venation pattern: Palmate. Texture, upper and lower surfaces: Glabrous, rough; leathery. Color: Developing and fully expanded foliage, upper surface: 146A; venation, 146B. Developing and fully expanded foliage, lower surface: 146B; venation, 146C. Zonation pattern: More prominent on developing leaves. Location of zone from margin: About 1.5 cm. Width of zone: About 2 cm. Color: 200B. Petiole: Length: About 3 cm. Diameter: About 2 mm. Texture, upper and lower surfaces: Pubescent; rough. Color, upper and lower surfaces: 147B.

Flower description:

*Flower arrangement.*—Bright red-colored flowers; single rotate flowers arranged in roughly hemispherical umbels arising from apical leaf axils. Umbels displayed above the foliage on strong peduncles. Flowers face upright to outwardly; flowers mostly flat. Flowers not persistent. Flowers not fragrant.

*Quantity of flowers.*—About twelve flower umbels per plant each umbel with about ten flower buds and open flowers.

*Flowering season.*—Year-round under greenhouse conditions. In Germany, flowering is continuous from May until frost.

*Flower longevity.*—Individual flowers last about six to ten days on the plant; umbels last about three to four weeks on the plant.

*Umbel height.*—About 5 cm.

*Umbel diameter.*—About 10 cm.

*Flower diameter.*—About 4.5 cm.

*Flower depth* (*height*).—About 1.5 cm.

*Flower buds.*—Length: About 1 cm. Diameter: About 5 mm. Shape: Elliptic. Color: 137D.

*Petals.*—Quantity per flower: About five. Length: About 2.7 cm. Width: About 2.3 cm. Shape: Obovate. Apex: Rounded. Base: Attenuate. Margin: Entire. Texture, upper and lower surfaces: Smooth, glabrous; velvety. Color: When opening and fully opened, upper surface: Darker than 45A; towards the base, close to 155D; venation, 59A. When opening and fully opened, lower surface: 46C; towards the base, close to 155D; venation, 59C.

*Sepals.*—Quantity per flower: About five in a single whorl. Length: About 1.3 cm. Width: About 4 mm. Shape: Lanceolate. Apex: Acute. Base: Attenuate. Margin: Entire. Texture, upper and lower surfaces: Pubescent. Color, upper surface: 146B. Color, lower surface: 146C.

*Peduncle* (*umbel stem*).—Length: About 10 cm. Diameter: About 3 mm. Strength: Strong. Texture: Sparsely pubescent. Color: 137D.

*Pedicel* (*individual flower stem*).—Length: About 3 cm. Diameter: About 1.5 mm. Strength: Strong. Texture: Pubescent. Color: 144A to 148A.

*Reproductive organs.*—Androecium: Stamen quantity per flower: About five to seven. Anther length: About 2 mm. Anther shape: Elongated. Anther color: 179B. Pollen amount: Abundant. Pollen color: 167A. Gynoecium: Pistil quantity per flower: One. Pistil length: About 3 mm. Stigma shape: Five-parted. Stigma color: 59A. Style length: About 1 mm. Style color: 56D. Ovary color: 138D.

*Seed.*—Shape: Elliptic. Length: About 4 mm. Diameter: About 1 mm. Color: Brownish.

Disease/pest resistance: Plants of the new Ivy *Geranium* have not been observed to be resistant to pathogens and pests common to Ivy *Geraniums*.

Garden performance: Plants of the new Ivy *Geranium* have been observed to tolerate rain, wind, and temperatures ranging from about 0° C. to about 35° C. and have demonstrated good garden performance.

It is claimed:

1. A new and distinct cultivar of Ivy *Geranium* plant named 'Pacharvel', as herein illustrated and described.

* * * * *

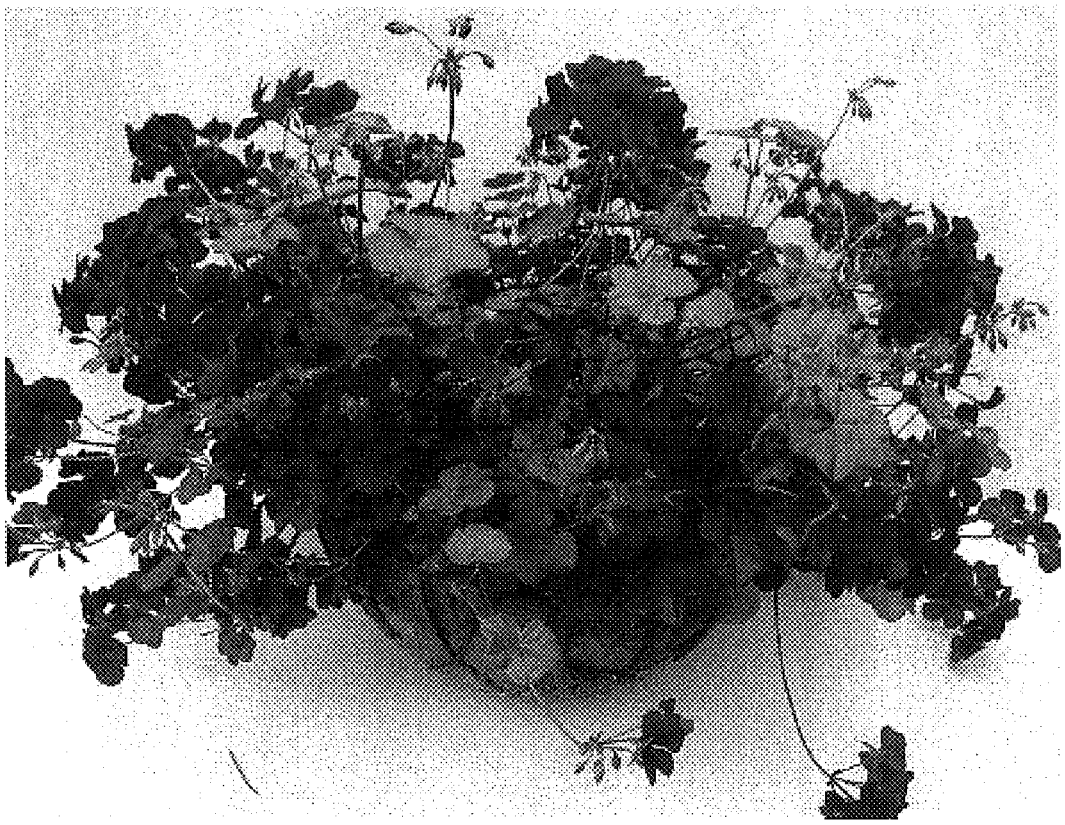

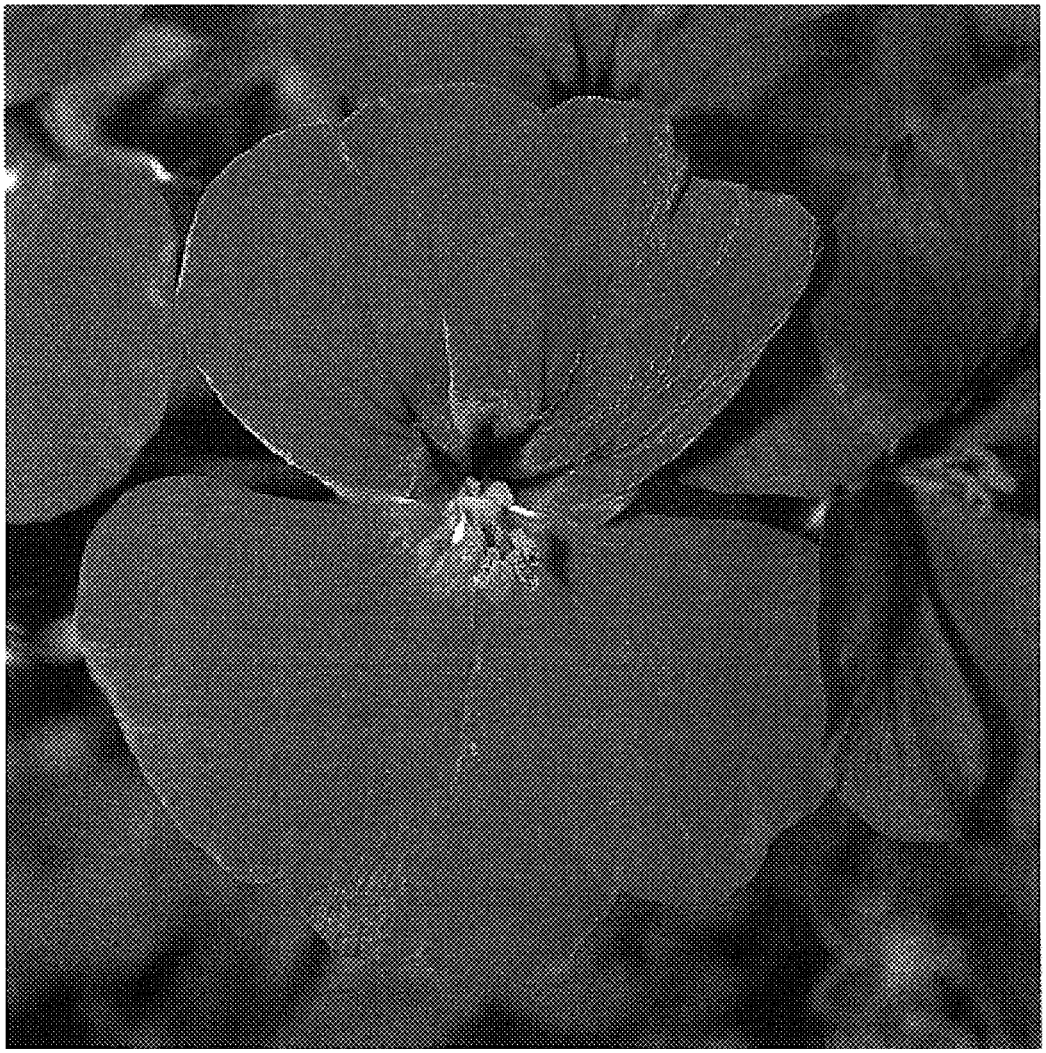

UNITED STATES PATENT AND TRADEMARK OFFICE

CERTIFICATE OF CORRECTION

PATENT NO. : PP 18,443 P2
APPLICATION NO. : 11/358873
DATED : January 22, 2008
INVENTOR(S) : Christa Hofmann It is certified that error appears in the above-identified patent and that said Letters Patent is hereby corrected as shown below:

The correct varietal denomination is 'Pachafvel'.

In an office mistake, the varietal denomination appears as 'Pacharvel' in the following nine (9) places:

Pacharvel should read Pachafvel

In the abstract. - line 2

Throughout the specification:

Col. 1, line 7 & 8;
Col. 1, line 17;
Col. 1, lines 30 & 31;
Col. 2, line 30;
Col. 2, line 32;
Col. 2, line 35; and
Col. 3, line 16.

In the claim col. 4 line 67

Signed and Sealed this

Third Day of February, 2009

John Doll

JOHN DOLL
*Acting Director of the United States Patent and Trademark Office*